United States Patent [19]

Chow et al.

[11] Patent Number: 4,482,345
[45] Date of Patent: Nov. 13, 1984

[54] AUTOMATED CONTROL FOR A TWO-DIRECTIONAL PUMP

[75] Inventors: Wing-Sun Chow, Upper Montclair, N.J.; Richard W. Walton, Middletown Township, Delaware County, Pa.; Donna A. D'Stefan, Plainsboro, N.J.

[73] Assignee: E. R. Squibb & Sons, Inc., Princeton, N.J.

[21] Appl. No.: 590,236

[22] Filed: Mar. 16, 1982

Related U.S. Application Data

[63] Continuation of Ser. No. 349,300, Feb. 16, 1982.

[51] Int. Cl.³ .................................................. A61M 37/00
[52] U.S. Cl. ..................................... 604/31; 604/67; 604/151
[58] Field of Search ..................... 604/27, 28, 30, 31, 604/65, 67, 131, 141, 151, 152, 154; 417/217, 211.5

[56] References Cited

U.S. PATENT DOCUMENTS 4,275,726 6/1981 Schael ................................ 604/31 X Primary Examiner—Edward M. Coven
Assistant Examiner—John C. Hanley
Attorney, Agent, or Firm—Lawrence S. Levinson; Sanford J. Asman

[57] ABSTRACT

A controller for a two-directional air pump, of the type used in performing medical experiments is described. The controller includes a level sensing apparatus which is used to initiate an electric signal which controls a pneumatic solenoid which toggles the two-directional pump. Using the apparatus, the Doluisio technique may be performed automatically.

7 Claims, 1 Drawing Figure

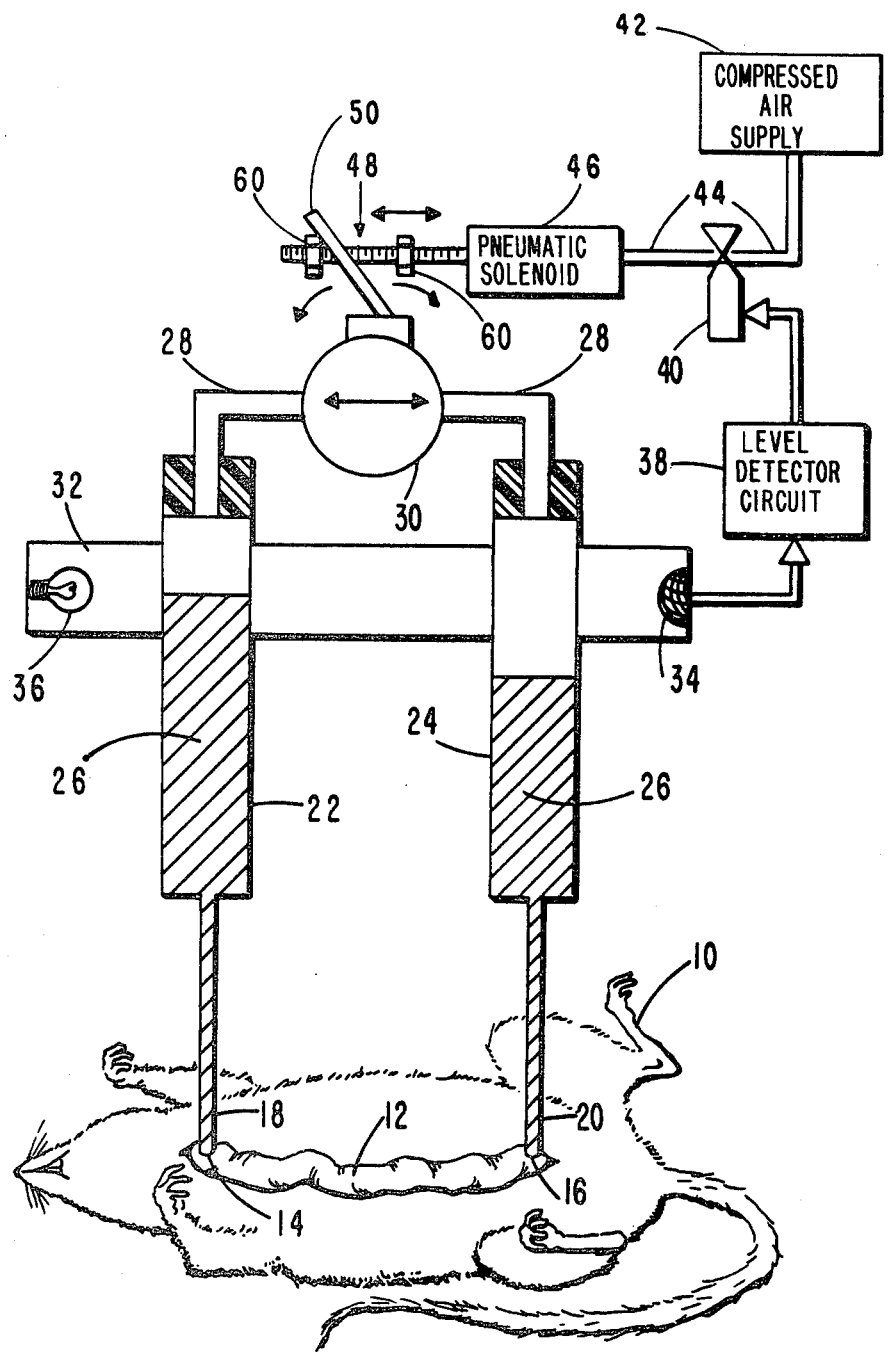

AUTOMATED CONTROL FOR A TWO-DIRECTIONAL PUMP

BACKGROUND OF THE INVENTION

This is a continuation of application Ser. No. 349,300, filed Feb. 16, 1982.

The present invention relates to an automatic control for a two-directional pump of the type used in pharmaceutical studies.

In testing drugs, one test which is performed relates to the rate of absorption of the drug through an intestinal wall. In the so-called Doluisio technique, a laboratory animal, such as a rat, has a portion of its intestine surgically moved to a position outside its body. A section of the exposed intestine has a glass cannula inserted into it at each end. Then, a syringe, containing the drug to be tested in solution, is connected through each cannula to the ends of the exposed intestine. The upper portion of each syringe is typically connected through rubber stoppers to a two-directional air pump, thereby creating a closed system. Thus, when air is pumped in one direction into a first syringe the fluid level in the first syringe goes down, and the fluid level rises in the opposite syringe.

In order to conduct an absorption study using the Doluisio technique, it is necessary for the individual performing the study to manually reverse the flow of the two-directional pump approximately every 5–20 seconds when the fluid level rises to a particular point in each syringe, thereby oscillating the drug solution in the animal's intestine.

The flow reversal is accomplished by changing the position of a toggle valve which has a lever handle on the end of a shaft. The operator reverses the air flow by toggling the valve.

It has been found that variations in operator technique can result in discrepancies in the results of the absorption tests. Accordingly, an automated approach to performing the switching operations in order to eliminate operator variations has been desired.

SUMMARY OF THE INVENTION

The present invention is an automatic apparatus used to automate the oscillation of a fluid which is contained within two columns which are connected at their lower ends. When the apparatus detects the rise of the fluid above a predetermined point, it automatically reverses the flow direction of a two-directional air pump connected to the tops of the columns, thereby causing the fluid to decline in one column while rising in the other column. The level to which the fluid will rise is controlled by a photocell which is adjusted to the desired height. In the preferred embodiment of the invention, both columns pass between the photocell and an associated light source.

BRIEF DESCRIPTION OF THE INVENTION

The sole FIGURE of the Drawing is a pictorial representation of the apparatus used in the present invention.

DETAILED DESCRIPTION OF THE PREFERRED EMBODIMENT

Referring generally to FIG. 1, a laboratory animal, such as a rat 10, which has had a portion of its gut exposed for the purpose of performing an absorption study is shown. Other animals, e.g. mice, rabbits, dogs, or monkeys may also be used in such studies. In a typical study involving a rat, approximately 15–35 cm of gut 12 will be exposed. Into each end 14, 16 of the exposed gut 12 L-shaped glass cannulas 18, 20 are inserted. Syringes 22, 24 are connected to the gut 12 through the cannulas 18, 20, respectively. The syringes contain a solution 26, on which the absorption study is being conducted. The syringes 22, 24 are connected through tubing 28 to a two-directional pump 30 which is used to pump air into alternate syringes in order to oscillate the flow of the solution 26 within the gut 12.

Prior to the present invention, when the solution 26 rose above a predetermined level in one of the syringes 22, 24, it was necessary for an operator to manually switch the lever handle 50 on the valve of the two-directional pump 30 to reverse the air flow of the pump 30 and force the solution 26 down in that syringe and up in the opposite syringe. The present invention, on the other hand, comprises a level sensing device 32 which is comprised, in the present invention, of a photocell 34 and a built in light source 36. The level sensing device 32 is capable of sensing the rise of solution in either syringe above a predetermined point corresponding to the interruption of the beam from the light source 36 to the photocell 34. In the preferred embodiment of the present invention, the level sensing device 32 is comprised of a Model SPC-41 Photocell and Light Source Assembly manufactured by Kraft Apparatus, Inc., 125-19 Liberty Avenue, South Richmond Hill, N.Y. 11419.

The level sensing device 32 sends an electrical signal to a level detecting circuit 38 any time the level of fluid 26 in either of the syringes 22, 24 rises above the predetermined level.

The level detector circuit 38 includes a Kraft Apparatus, Inc. Liquid Level Control. The circuit 38 operates in conjunction with the level sensing device 32 described above. The level detector circuit 38 includes a switched power receptacle which delivers line power of 115 VAC through normally open relay contacts contained within the level detector circuit 38. When liquid, which may be either clear or opaque, obstructs the light path of the photocell 34, the level detector circuit 38 causes its internal relay to close, thereby reversing the relay contact position and causing power to be delivered to the receptacle. The level detector circuit 38 further comprises a latching memory device, such as a flip-flop, the output of which is connected to an electro-pneumatic solenoid 40.

Thus, each time the level detector circuit 38 receives a pulse from the level sensing device 32, it will alternately open and close the electro-pneumatic solenoid 40. In the preferred embodiment of the invention, the electro-pneumatic solenoid 40 is an Asco Model 8342B2 solenoid manufactured by Automatic Switch Company, Hanover Road, of Florham Park, N.J. The solenoid 40 operates to control the flow of compressed air from a supply 42 through an air line 44 to a piston in a pneumatic cylinder 46. In the preferred embodiment of the invention, the compressed air supply 42 provides air at a pressure of about 20 lbs. per square inch to the piston. In the preferred embodiment of the invention, the pneumatic cylinder 46 is a Sheffer pneumatic cylinder. When the pneumatic cylinder 46 is operated, its piston rod 48 moves the lever handle 50 of the reversing switch of the two-directional air pump 30, and reverses the flow direction of the air in two-directional air pump 30. The rate of flow of air increases as the lever handle 50 is moved away from its center position. Consequently, oscillatory flow of the solution 26 between the syringes 22, 24 is automatically regulated as to rate and direction, its being understood that when the system is turned on the pump 30 is adjusted to force air into the cylinder having the higher level.

As will be understood by those skilled in th art, the present invention may be used in conjunction with other vertical columns containing liquids. It can also be used with animals other than rats. The frequency of the oscillation can be adjusted by varying the rate of flow of air through the two-directional air pump 30, as the air flow rate of the pump 30 is proportional to the displacement from the center position of the lever handle 50 attached to the piston rod 48. In the operation of the preferred embodiment of the invention, the maximum displacement of the lever handle 50 can be adjusted by changing the position of retaining means on the piston rod 48 such as locking nuts 60. The locking nuts 60 are threaded on the piston rod 48, on either side of the lever handle 50, and they limit the travel of the lever handle 50.

We claim:

1. In a system comprising a two-directional air pump having a reversible input and output connected to a pair of vertical columns adapted to hold liquid and to be attached to one another through a communicating passage at their lower ends whereby a closed loop will be formed by said vertical columns, said pump, and said communicating passage, a valve having lever handle means for reversing the input and output of said pump to direct air from said pump into alternating ones of said vertical columns whereby liquid within said vertical column into which air is being pumped will decline while liquid in the other vertical column rises when said columns are attached to one another through a communicating passage, the improvement comprising an automatic control for said system comprising:

(a) level sensing means for sensing the liquid level in either of said verticle columns rising above a predetermined level;
    (b) a supply of compressed air;
    (c) an electro-pneumatic solenoid means connected to said supply of air for controlling the flow of air from said supply;
    (d) a circuit means connected to said level sensing means for alternately opening and closing said electro-pneumatic solenoid each time said level sensing means senses a predetermined liquid level in either of said columns;
    (e) a pneumatic cylinder having a piston with a piston rod connected to said lever handle, said cylinder being connected in such a way that said piston is responsive to said flow of air from said supply, whereby said lever handle is alternately switched in position in response to the liquid level in either of said columns rising above a predetermined level causing said liquid to flow back and forth in said communicating passage between said vertical columns.

2. The apparatus of claim 1 wherein a portion of each said columns is transparent.

3. The apparatus of claim 2 wherein said level sensing means comprises a photocell and a light source.

4. The apparatus of claim 3 wherein the said vertical columns are adapted to be attached to the intestine of an animal.

5. The apparatus of claim 4 wherein said vertical columns are adapted to be attached to the intestine of an animal selected from the group of animals consisting of mice, rats, dogs, rabbits, and monkeys.

6. The apparatus of claim 3 wherein the piston rod includes retaining means on either side of said lever handle.

7. The apparatus of claim 6 wherein said piston rod includes a threaded portion and said retaining means comprises nuts screwed thereon.

* * * * *